US 7,326,053 B2

(12) United States Patent
Berger et al.

(10) Patent No.: US 7,326,053 B2
(45) Date of Patent: Feb. 5, 2008

(54) DENTAL ROOT CANAL APEX MEASURING APPARATUS AND METHOD

(75) Inventors: Nachman Berger, Ramut Gan (IL); Gabriel Savin, Rishon LeZion (IL); Haim Rosenboim, Netanya (IL); Avigail Anca Rosenboim, Netanya (IL)

(73) Assignee: Medic.NRG Ltd., Kibbutz Afikim (IL)

( * ) Notice: Subject to any disclaimer, the term of this patent is extended or adjusted under 35 U.S.C. 154(b) by 50 days.

(21) Appl. No.: 11/355,814

(22) Filed: Feb. 16, 2006

(65) Prior Publication Data

US 2006/0184061 A1 Aug. 17, 2006

(30) Foreign Application Priority Data

Feb. 17, 2005 (IL) .................................. 166949

(51) Int. Cl.
*A61C 3/00* (2006.01)
*A61C 19/00* (2006.01)
*A61C 19/04* (2006.01)
*A61B 5/103* (2006.01)

(52) U.S. Cl. .................... 433/72; 433/32; 600/587; 600/590

(58) Field of Classification Search ............... 600/590, 600/589, 587, 547; 443/27, 32, 72, 224
See application file for complete search history.

(56) References Cited

U.S. PATENT DOCUMENTS

| 5,080,586 | A | 1/1992 | Kawai |
| 5,096,419 | A | 3/1992 | Kobayashi et al. |
| 5,759,159 | A | 6/1998 | Masreliez |
| 6,221,031 | B1 | 4/2001 | Heraud |
| 6,425,875 | B1 | 7/2002 | Reifman et al. |
| 2004/0158169 | A1 | 8/2004 | Lewallen et al. |
| 2004/0225234 | A1 | 11/2004 | Siemons |

*Primary Examiner*—Max F. Hindenburg
*Assistant Examiner*—Jonathan M Foreman
(74) *Attorney, Agent, or Firm*—Milde & Hoffberg, LLP

(57) ABSTRACT

Apparatus for determining the apex of a dental root canal in a tooth includes a software operated microcontroller having a pulse generator, a memory and an analog to digital converter (ADC), the pulse generator feeding pulses to a gain control circuit for controlling the amplitude of the pulses. The apparatus also includes a driver receiving signals from the control circuit for feeding the signals to an electrically conductive shaft having a leading edge and a dental instrument connectable thereto, an input buffer receiving signals from the dental instrument and feeding the signals to the ADC, and a display for exhibiting data concerning the distance of the leading edge of the shaft from the root canal apex. A method for determining the apex of a dental root canal in a tooth is also provided.

5 Claims, 2 Drawing Sheets

DENTAL ROOT CANAL APEX MEASURING APPARATUS AND METHOD

BACKGROUND OF THE INVENTION

The present invention relates to dental apparatus and method and more particularly the invention is concerned with dental root canal apex measuring apparatus and method.

In root canal therapy, a dental probe, such a as a reamer or a file, is inserted into the canal and manipulated to remove undesired material. A flexible filler substance is then placed in the root canal that is sealed with rigid material. If the canal is not completely cleaned prior to filling and sealing, debris left inside the canal can prevent proper healing. The probe must therefore be inserted all the way to the apex of the root canal during cleaning to remove all debris. If, however, the probe is inserted too deeply, the tool penetrates the jaw tissue, causing swelling and unnecessary trauma for the patient. It is therefore essential to precisely determine when the probe tip has reached the root canal apex, so that the canal can be cleaned fully, without excessive trauma to the patient.

Locating the apex is difficult, because the narrow canal does not provide a clear viewing path and fluids can partially fill the canal. In one method, the probe is inserted into the canal and the tooth is X-rayed. In the X-ray image, the metal probe contrasts with the surrounding tooth and body tissue, so that the positions of the probe tip and the apex can be compared. If the probe tip is not at the apex, it is inserted deeper into the canal and a new X-ray image is obtained. This method is unreliable, time-consuming, costly, and exposes the patent to unnecessary X-ray radiation.

It is also known to locate the root apex by inserting a conductive probe into the root canal and placing an electrode in contact with the patient's body, usually in or near the mouth. As the probe is moved through the canal towards the apex, electrical measurements across the probe and electrode are made.

Examples of this latter method are described in several U.S. Patents.

U.S. Pat. No. 5,080,586 discloses locating the apex by making impedance measurements by driving two fixed frequencies and fixed amplitude sinus shape current as the probe is moved towards the apex. A detector determines that the probe tip is at the apex when the difference of the two impedance measurements is within a predetermined range. The device measures peak volt.

U.S. Pat. No. 5,096,419 discloses the apex by making impedance measurements by driving two fixed frequencies and fixed amplitudes sinus shape current as the probe is moved towards the apex. A detector determines that the probe tip is at the apex when the ratio of the two impedance measurements is within a predetermined range. The device measures a peak volt.

U.S. Pat. No. 6,425,875 discloses locating the apex by making impedance measurements by driving two fixed frequencies and fixed amplitude sinus shape current as the probe is moved towards the apex. A detector determines that the probe tip is at the apex by a defined Region A and a defined Region B. At Region A, the difference of the two impedances defines the location of the probe tip. In contrast, at Region B the ratio of the two impedances defines the location. The device measures RMS volts and can control the output impedance.

SUMMARY OF THE INVENTION

It is a principle object of the present invention to provide a dental root canal apex measuring apparatus and method utilizing low power, thus decreasing the patient's discomfort.

It is a further object of the present invention to provide a dental root canal apex measuring apparatus and method having an improved signal to noise ratio, hence improved accuracy.

In accordance with the present invention there is therefore provided an apparatus for determining the apex of a dental root canal in a tooth, comprising a software operated microcontroller having a pulse generator, a memory and an analog to digital converter (ADC); said pulse generator feeding pulses to a gain control circuit for controlling the amplitude of said pulses; a driver receiving signals from said control circuit for feeding said signals to an electrically conductive shaft having a leading edge and a dental instrument connectable thereto; an input buffer receiving signals from said dental instrument and feeding said signals to said ADC, and a display for exhibiting data concerning the distance of the leading edge of said shaft from the root canal apex.

The invention further provides a method for determining the apex of a dental root canal in a tooth, comprising providing a software operated microcontroller having a pulse generator, a memory and an analog to digital converter (ADC); said pulse generator feeding pulses to a gain control circuit for controlling the amplitude of said pulses; a driver receiving signals from said control circuit for feeding said signals to an electrically conductive shaft having a leading edge and a dental instrument connectable thereto; an input buffer receiving signals from said dental instrument and feeding said signals to said ADC; a display for exhibiting data concerning the distance of the leading edge of said shaft from the root canal apex; attaching the driver to said shaft and to a tissue of a patient; inserting said shaft in a root canal, sending a plurality of test pulses through said shaft and calculating the power of each of said several pulses; determining a medial estimate reference power based on the calculated power of each of said pulses, and determining the location of the shaft's edge relative to the canal apex by means of precalculated data pairs exhibiting the distance between the shaft's edge and the canal apex and said reference power.

For a full understanding of the present invention, reference should now be made to the following detailed description of the preferred embodiments of the invention as illustrated in the accompanying drawings.

DETAILED DESCRIPTION OF THE PREFERRED EMBODIMENTS

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Figure 1:
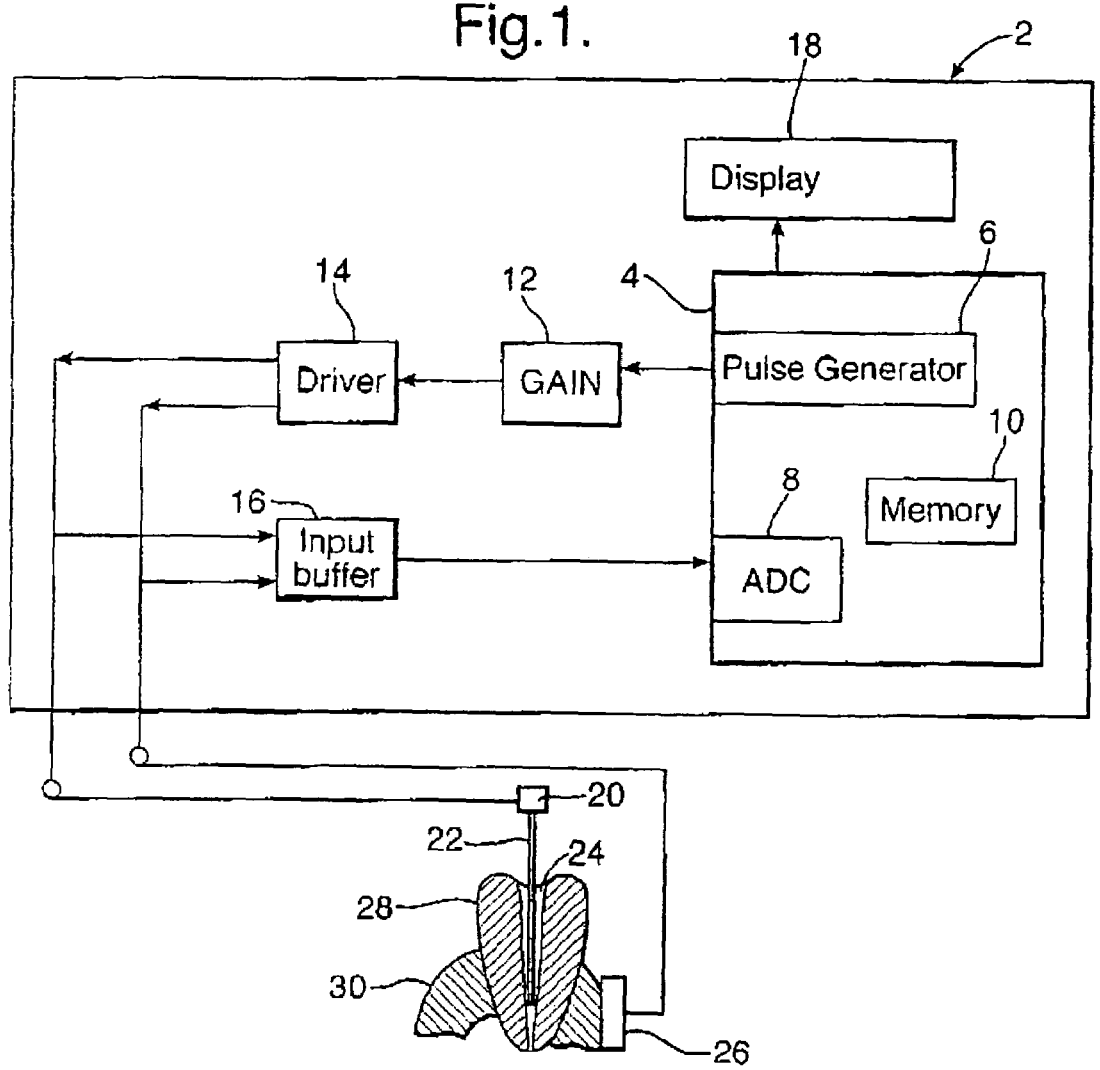
FIG. 1 is a block diagram of a preferred embodiment of the dental root canal apex measuring apparatus, according to the invention.

The dental root canal apex measuring apparatus 2, according to the present invention illustrated in FIG. 1, includes a microcontroller 4 comprising a pulse generator 6, an analog to digital A/D converter (ADC) 8 and a memory 10. The generator 6 sends pulses through a gain control 12 to a driver 14, the output of which leads to an input buffer 16 feeding the ADC 8. A display 18 is connected to the microcontroller 4 and operated thereby. The output from the apparatus 2 is connectable to a conductive canal dental instrument 20 having a shaft 22 inserted in a tooth root canal 24 and an electrode 26, respectively, connectable with a tooth 28 and a gum tissue 30 adjacent the tooth of a patient. The electrode 26 can just as well be connected to the patient's lip or any other part of the body.

Figure 2A:
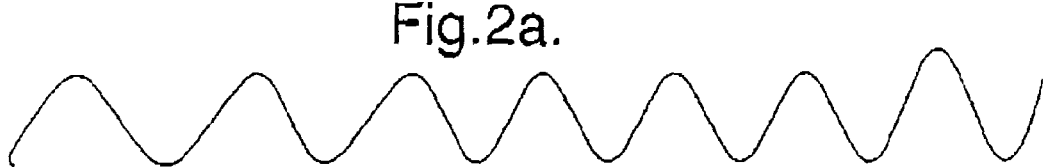
FIG. 2 is a schematic representation of the pulses generated by the apparatus of FIG. 1, as compared with the prior art pulses.
Figure 2B:
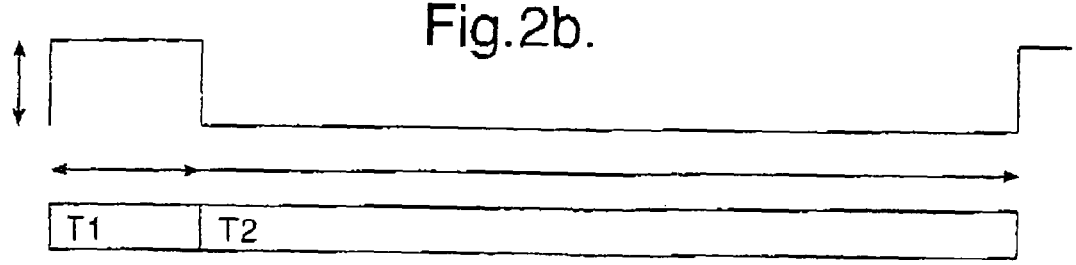

Referring now also to FIG. 2, there are depicted at a) a prior art continuous sine wave (single frequency) and at b) a square wave (multi-frequency), or a substantially square wave pulse, extending over an active period of time T1 and a non-active period of time T2, between two consecutive pulses T1.

Prior art apex locator's impedance measurements are effected by applying to the tissue a continuous sinus-shaped current at one or more frequencies. Due to the fact that current is limited by regulation and patient comfort, the current restriction limits the device's accuracy. For example, in case of continuous sinus, the power is P=A/1.44. In case of individual pulses, e.g., square pulses, the power is P=A·T1/(T1+T2). If the current amplitude is A=10 µA, T1 is 10 microseconds and T2 is 90 microseconds, for continuous sinus signal, the power is P=7 µA and for a non-continuous pulse, the power P=10·10/(10+90)=1 µA. Hence, the use of non-continuous pulses to drive the tissue, reduces the current dramatically and can increase the measurement accuracy.

Figure 3:
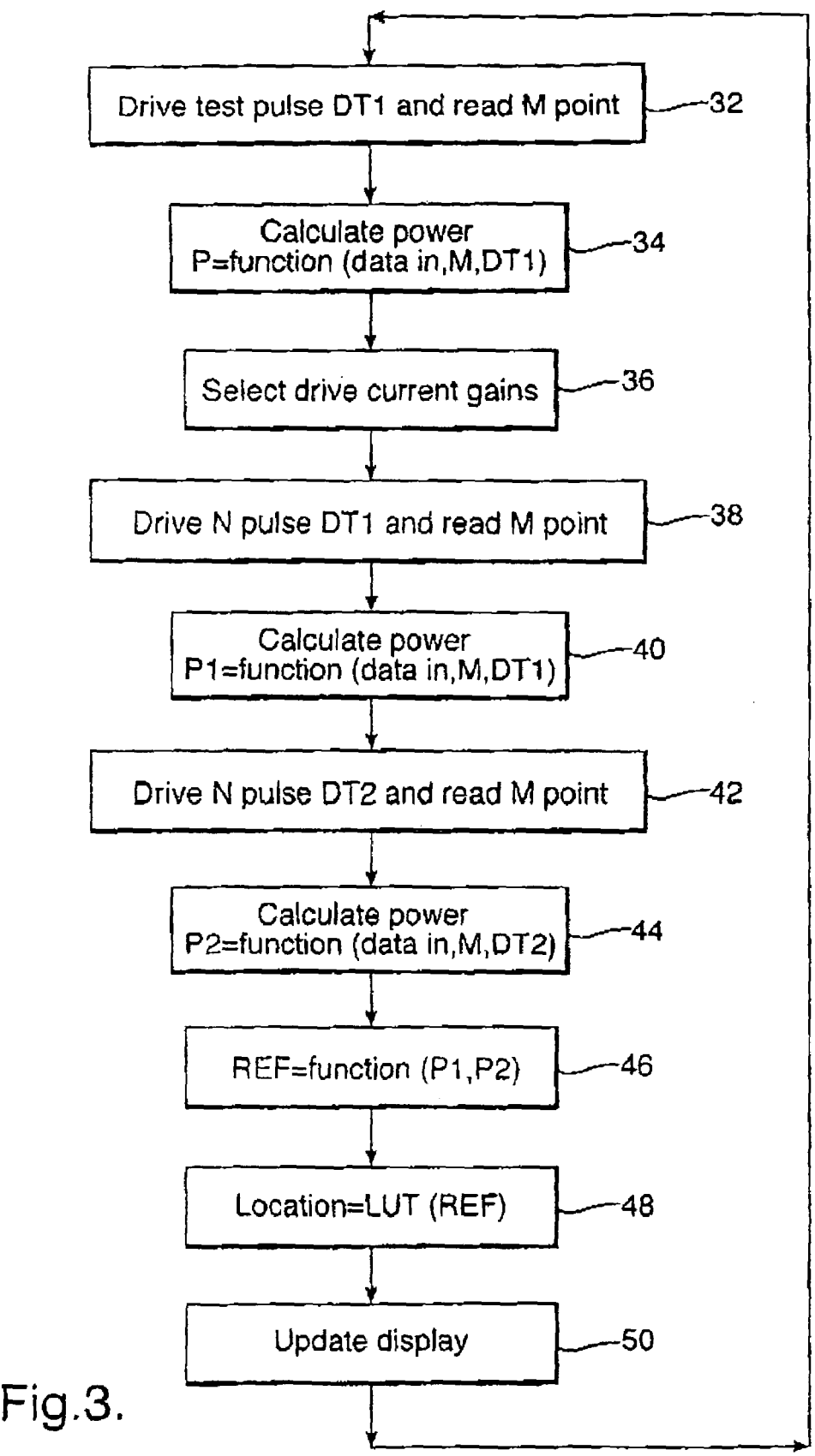
FIG. 3 is a flow diagram of the method according to the present invention.

The operation of the apparatus 2 will now be described also with reference to FIG. 3. The microcontroller's 4 software controls the operation of the apparatus 2 according to an internal program memory. It repeats the measurement cycle, e.g., each 200 millisecond, as shown in FIG. 2. The microcontroller 4 sends to the pulse generator 6 a short period pulse of active time T1. The non-active time between two consecutive pulses T1, is a time period of T2. The microcontroller also optionally controls a variable output amplitude by the gain control 12. During the time the microcontroller 4 drives the shaft 22 of a dental instrument 20 in the canal 24, the ADC 8 advantageously, continuously sends N pulses and samples M points along the canal 24 and stores signals in the microcontroller's memory 10. The microcontroller 4 uses the data located in the memory 10, to calculate and determine the position of the shaft in the canal, updates information and displays it on the display 18. In order to select the proper gain of the pulse generated by the pulse generator 6, the software actuates a test pulse (32, FIG. 3) of an active time DT1, which for example, can be 760 microseconds, and by using digital filters, it calculates at 34, the power of the signal [p=function (data in, M, DT1)]. Data in, M, DT1 refers to input data vector, number of sampling points and pulse active time, respectively. The software effects the selection of the drive current gain at 34 according to a list of thresholds stored in the program. This gain will be set for each measurement cycle at 36. Using the adaptive gain, the apparatus is keeping a constant signal to noise ratio regardless of the instruments environment, i.e., dry canal, wet canal, etc. The software drives the pulse DT1 at a specific gain for an active time T1, at 38, and calculates the power of the signal and stores it in a memory location designated P1 (see 40). Subsequently at 42, the software drives pulse DT2 and calculates the power of the signal and stores it in a memory at a location designated P2 (see 44). Based on the power measurements performed at e.g., DT1 and DT2 an average, mean, or any other selected medial estimate power is calculated at 44. The calculated power referred to as the REF power is read at 46 against the location of the shaft's edge in the canal 24, in a Look Up Table (LUT), at 48. The LUT is generated according to laboratory and clinical tests previously performed. The LUT determines the location of the shaft's edge relative to the canal apex, by means of pre-calculated data pairs exhibiting the distance between the shaft's edge and the canal apex and said REF power. The software then updates the function at 50 and displays it on the display 18 (FIG. 1) and then starts a new cycle at 32.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An apparatus for determining the apex of a dental root canal in a tooth of a patient, said apparatus comprising a dental instrument having an electrically conductive shaft with a leading edge adapted for insertion in the root canal, said apparatus further comprising, in combination:

a gain control circuit;

a software operated microcontroller having a memory, an analog-to-digital converter (ADC) and a square wave pulse generator;

said pulse generator producing a pulse signal having square wave pulses with a first period ($T_1$) separated by an inactive, second period ($T_2$) which is longer than said first period ($T_2 > T_1$), and supplying said pulse signal to said gain control circuit which controls the amplitude of said pulses;

a driver receiving said pulse signal from said gain control circuit and supplying said pulse signal to said electrically conductive shaft, said dental instrument having an electrode connectable with tissue of the patient;

an input buffer receiving signals from said electrode of said dental instrument and supplying said signals to said ADC;

the software of said microcontroller performing measurements of the power of said pulse signal and calculating a medial estimate of power; and a display, coupled to said microcontroller, for exhibiting said medial estimate of power and displaying data concerning the distance of the leading edge of said electrically conductive shaft from the apex of the root canal.

2. The apparatus as claimed in claim 1, further comprising a first electrode connectable to said dental instrument and a second electrode connectable to a tissue of a patient.

3. A method for determining the apex of a dental root canal in a tooth, said method comprising the steps of:
providing a software operated microcontroller having a pulse generator, a memory and an analog to digital converter (ADC); said pulse generator feeding pulses to a gain control circuit for controlling the amplitude of said pulses; a driver receiving signals from said control circuit for feeding said signals to an electrically conductive shaft having a leading edge and a dental instrument connectable thereto; an input buffer receiving signals from said dental instrument and feeding said signals to said ADC; a display for exhibiting data concerning the distance of the leading edge of said shaft from the root canal apex;
attaching the driver to said shaft and to a tissue of a patient;
inserting said shaft in a root canal;
sending a plurality of test pulses through said shaft and calculating the power of each of said several pulses;
determining a medial estimate reference power based on the calculated power of each of said pulses, and
determining the location of the shaft's edge relative to the canal apex by means of pre-calculated data pairs exhibiting the distance between the shaft's edge and the canal apex and said reference power.

4. The method as claimed in claim 3, wherein said pulses are substantially square pulses.

5. The method as claimed in claim 3, further comprising the step of selecting drive current gain prior to applying the pulses to said shaft for keeping a constant signal to noise ratio.

* * * * *